United States Patent [19]
Bauer et al.

[11] Patent Number: 5,688,776
[45] Date of Patent: Nov. 18, 1997

[54] CROSSLINKED POLYSACCHARIDES, PROCESS FOR THEIR PREPARATION AND THEIR USE

[75] Inventors: Kurt Heinz Bauer, Freiburg; Juergen Betzing, Aachen, both of Germany

[73] Assignee: BASF Aktiengesellschaft, Ludwigshafen, Germany

[21] Appl. No.: 302,831

[22] PCT Filed: Feb. 1, 1993

[86] PCT No.: PCT/EP93/00225

§ 371 Date: Sep. 16, 1994

§ 102(e) Date: Sep. 16, 1994

[87] PCT Pub. No.: WO93/19095

PCT Pub. Date: Sep. 30, 1993

[30] Foreign Application Priority Data

Mar. 20, 1992 [DE] Germany .............. 42 09 160.8

[51] Int. Cl.⁶ .............. A61K 31/715; C08B 37/06; C08B 37/02; C08B 37/00
[52] U.S. Cl. .............. 514/54; 514/59; 536/2; 536/104; 536/106; 536/112; 536/114; 536/123.1; 536/123.12
[58] Field of Search .............. 536/2, 104, 106, 536/112, 114, 123.1, 123.12; 514/54, 59

[56] References Cited

U.S. PATENT DOCUMENTS

| | | | |
|---|---|---|---|
| 3,615,794 | 10/1971 | Nimerick | 523/130 |
| 4,143,007 | 3/1979 | DeMartino | 524/55 |
| 4,960,876 | 10/1990 | Molteni et al. | 536/114 |

FOREIGN PATENT DOCUMENTS

| | | |
|---|---|---|
| 095968 | 12/1983 | European Pat. Off. |
| WO9116881 | 11/1991 | WIPO |

OTHER PUBLICATIONS

Chemical Abstracts, vol. 106, No. 1, abstract 106:5355m (1987).
Am. Quim. Ser. C, vol. 82, No. 1 (1986), Spain, pp. 37–45.
Polymer Preprints, vol. 30, No. 1, 1989, U.S.A., pp. 480–481.

*Primary Examiner*—John Kight
*Assistant Examiner*—Everett White
*Attorney, Agent, or Firm*—Keil & Weinkauf

[57] ABSTRACT

The invention relates to polysaccharides which are crosslinked with bifunctional crosslinkers and are no longer water-soluble but are still biodegradable, have a swelling of from 100 to 1000%, where the swelling, which means the percentage gain in weight, is determined by the following equation:

$$A = \frac{W_t - W_o}{W_o} \times 100$$

in which A is the percentage gain in weight, $W_o$ is the weight of the dry polymer and $W_t$ is the weight of the swollen polymer saturated with water. It likewise relates to a process for preparing the crosslinked polysaccharides and to the use of the crosslinked polysaccharides for coating and/or embedding medicinal active substances or drug compositions. The invention furthermore relates to a drug which contains an active substance which acts in the large intestine or an active substance which is broken down on passing through the stomach or small intestine, coated with or embedded in one of the crosslinked polysaccharides.

6 Claims, No Drawings

CROSSLINKED POLYSACCHARIDES, PROCESS FOR THEIR PREPARATION AND THEIR USE

DESCRIPTION

The invention relates to polysaccharides cross-linked with bifunctional crosslinkers, to a process for their preparation, to their use for coating and embedding drugs and to drugs coated and embedded using them.

The oral dosage form is a preferred administration of drugs. Drugs which do not act until the large intestine, eg. those employed for chronic inflammations of the large intestine or Crohn's disease, and drugs which are normally broken down or digested under physiological conditions in the stomach or in the small intestine or must be protected in order for them to reach the large intestine unchanged. Examples of medicinal substances which are broken down or digested in the small intestine include peptide medicinal substances.

There is therefore a need for a film coating and an embedding material by which, on oral administration, the administered active substance is protected on transport through the body as far as the large intestine and is then released there. Peptide medicinal substances could thus be protected, on oral use, from decomposition by gastric fluid as well as from decomposition by peptidases. Since the peptidase activity in the large intestine is only very low but the absorption of peptides takes place in the large intestine, this would be an acceptable way to administer peptide medicinal substances.

Owing to the natural physiological pH gradient between saliva and stomach on the one hand, and stomach and small intestine on the other hand, it is now possible without special difficulties to develop drug forms which release their active substances specifically in the stomach or in the small intestine. This is achieved by embedding or coating drugs with ancillary substances which are soluble or resistant at the appropriate pH values.

Since, however, there is only little difference between the pH values on passing from the small intestine into the large intestine, for targeting the large intestine it is necessary to look for other utilizable physiological differences which can be used to achieve small-intestine resistance and large-intestine degradability. The successful development of novel small-intestine resistant but large-intestine degradable ancillary substances has not to date succeeded in opening up possibilities to be implemented for targeting the large intestine.

DE 40 06 521 A1 (and European Patent Application 450 176 A1 which corresponds to it) describes sugar-containing polymers for coating and embedding medicinal substances. These sugar-containing polymers are used to coat and/or embed pharmaceutical active substances which can be administered orally and result in the active substances which are contained in the polymers not being released until the large intestine. The polymers described in this publication have the disadvantage that they need complicated preparations and are crosslinked with polyisocyanates.

Numerous review articles recently have referred to the possibilities of absorption in the large intestine (M. L. G. Gardner (1988): Gastrointestinal absorption of intact proteins, Ann. Rev. Nutr. 8, 329–350; P. Gruber, M. A. Longer and J. R. Robinson (1987): Some Biological issues in oral controlled drug delivery, Adv. Drug Deliv. Rev. 1, 1–18; T. T. Karrarly (1989): Gastrointestinal absorption of drugs, Crit. Rev. 6 (1), 39–86).

Studies on administrations of medicinal substances into the large intestine have also been published and refer to the suitability of this region not only as target organ for topically active medicinal substances but also absolutely as absorption site. Thus, P. R. Bieck (1987, Arzneistoffresorptionen aus dem menschlichen Dickdarm—neue Erkenntnisse, Acta Pharm. Technol. 33 (3), 109–114) describes how several medicinal substances introduced into the large intestine via tubes or by means of controlled release HF capsules, including the β-receptor blockers oxprenolol and metoprolol as well as isosorbide 5-mononitrate, are absorbed virtually just as well as from the small intestine.

The present invention is based on the object of providing crosslinked polysaccharides, process for their preparation, their use and drugs, with which protected transport of medicinal substances through the stomach and small intestine is possible with subsequent targeted release of the medicinal substance in the large intestine. The intention according to the invention is to make possible local administration of medicinal substances in the large intestine, eg. in the case of chronic inflammations of the large intestine or Crohn's disease, and of active substances which are normally broken down or digested under the physiological conditions in the stomach or small intestine. The intention of the present invention is to open up the development of novel small-intestine resistant but large-intestine degradable ancillary substances for targeting the large intestine.

The Applicant has found that the small microbial colonization of the distal sections of the small intestine compared with the well-developed microflora in the cecum is particularly suitable for developing substances which make it possible to achieve the stated object.

The Applicant has found that certain crosslinked polysaccharides are suitable, by reason of their enzymatic degradability by the microflora of the large intestine, for use as film formers for developing novel drug forms which are soluble in the large intestine. Because of the enzymatic degradability by the bacterial cultures in the large intestine, the medicinal substances are specifically released there.

The invention relates to polysaccharides which are crosslinked with bifunctional crosslinkers and are no longer water-soluble but are still biodegradable, have a swelling of from 100 to 1000%, where the swelling, which means the percentage gain in weight, is determined by the following equation:

$$A = \frac{W_t - W_o}{W_o} \times 100$$

in which A is the percentage gain in weight, $W_o$ is the weight of the dry polymer and $W_t$ is the weight of the swollen polymer saturated with water.

The invention furthermore relates to a process for preparing the crosslinked polysaccharides, according to which a polysaccharide with a molecular weight of from 100,000 to 10 million, specifically Galactomannans: 100,000–1 million, preferably 500,000–1 million Laminarin: 100,000–1 million, preferably 500,000–1 million Glucomannan: 100,000–1 million, preferably 500,000–1 million Dextran: 100,000–10 million, preferably 1 million–10 million Pectins: 100,000 –500,000
Arabinogalactan: 100,000–300,000
Xylan: 100,000–500,000, is suspended in an aliphatic diglycidyl ether, a $C_4$–$C_{10}$-aliphatic dicarboxylic acid or its reactive derivative or a $C_4$–$C_{10}$-aliphatic dialdehyde with or without the addition of an inert organic solvent or swelling agent, the suspension is heated to a temperature in the range from room temperature to 80° C., a catalytic amount of a base is added to the suspension, the reaction mixture is stirred at the stated temperature for a period of from 1 to 15 hours, and subsequently the crosslinked polysaccharide is separated off in a manner known per se and washed where appropriate one or more times with water, methanol or acetone.

The invention likewise relates to the use of the crosslinked polysaccharides for coating and/or embedding medicinal active substances or drug compositions and to a drug which contains an active substance which acts in the large intestine or an active substance which is broken down on passing through the stomach or small intestine, coated with or embedded in one of the crosslinked polysaccharides.

The Applicant has surprisingly found that crosslinked polysaccharides which, in the uncrosslinked state, are broken down by the glycosidases of the large intestine microflora and which have been crosslinked with bifunctional crosslinkers in such a way that they are just no longer soluble in water but still biodegradable comply with the stated requirements. If derivatization is too extensive the degradability is lost. Accordingly, the polysaccharide may be modified according to the invention only just enough to suppress the solubility in water. This is done by crosslinking the polysaccharides with suitable crosslinkers. It must be noted in this connection that short crosslinking times and the use of long-chain crosslinkers result in correspondingly loose networks into which the enzyme can penetrate and break down the film enzymatically.

Polysaccharides which can be used according to the invention as starting points for the crosslinkings are listed in the following table.

Table of polysaccharides used according to the invention

| Poly-saccharide | Building block | Degradability | Mode of degradation |
| --- | --- | --- | --- |
| Galacto-mannan | (1,4)-β-mannose (1,6)-α-galactose | +++ | Endoenzyme Degradation products: Oligosaccharides |
| Laminarin | (1,3)-β-glucose | +++ | Exoenzyme Degradation products: Oligosaccharides |
| Pectins | (1,4)-α-galacturonic acid (partial methyl ester) | +++ | Exoenzyme Degradation products; Mono-, disaccharides |
| Gluco-mannan | (1,4)-β-mannose (1,4)-β-glucose | +++ | Endoenzyme Degradation products: Oligosaccharides |
| Arabino-galactan | arabinose galactose | +++ | |
| Xylan | (1,4)-β-xylopyranose | ++ | Exoenzyme Degradation products: Mono-, disaccharides |
| Dextran | branched glucans: α-1,6-D-glucose, α-1,3-glucose (branched) | +++ | Exoenzyme/ Endoenzyme |

The preferred polysaccharides among those listed in the table are galactomannan, glucomannan and dextran. Galactomannan is particularly preferred. The polysaccharides used according to the invention have a molecular weight of from 100,000 to 10 million. The molecular weight is not particularly critical as long as the abovementioned conditions are met, that is to say the polysaccharides are, in the uncrosslinked state, broken down by the glycosidase of the large intestine microflora and are no longer soluble in water after crosslinking. The preferred and particularly preferred molecular weights for some of the polysaccharides are indicated below.

Galactomannans: 100,000–1 million, preferably 500,000–1 million

Laminarin: 100,000–1 million, preferably 500,000–1 million

Glucomannan: 100,000–1 million, preferably 500,000–1 million

Dextran: 100,000–10 million, preferably 1 million–10 million

Pectins: 100,000–500,000

Arabinogalactan: 100,000–300,000

Xylan: 100,000–500,000

Suitable polysaccharides are broken down by enzymes. The endoenzyme (1,4)-β-mannase is demonstrably produced by the flora of the human large intestine.

Furthermore there are copious numbers of the bacterial genus Bacteroides present in the human large intestine, which genus produces an exo/endoenzyme system which breaks down α-1,6-glycosidic linkages which are present, for example, in dextran. This explains why the large intestine microflora is able to cleave not only β-1,4- but also α-1,6-glycosidic linkages. The polysaccharides used according to the invention are not attacked by amylases and are thus stable in the small intestine.

The crosslinked polysaccharides which are preferably used are those cleaved by endoenzymes. The endoenzymes cleave the polysaccharides in the interior and relatively rapidly, leading to immediate release of the active substance. The cleavage takes place slower with exoenzymes which attack the end of the polysaccharides.

The said polysaccharides are not suitable in the uncrosslinked formas film coating or embedding material because they are water-soluble and are dissolved and broken down too rapidly. They are therefore crosslinked according to the invention.

Various reagents can be used as crosslinkers according to the invention. The crosslinkers which are preferably used are those already employed and regarded as acceptable in pharmacology. The crosslinkers must be bifunctional, and examples are: aliphatic diglycidyl ethers such as 1,4-butanediol diglycidyl ether or 1,6-hexanediol diglycidyl ether, $C_1$–$C_4$-aliphatic dicarboxylic acids such as succinic acid, glutaric acid, adipic acid or their reactive derivatives such as the acid dichlorides or anhydrides, $C_4$–$C_{10}$-aliphatic dialdehydes such as, for example, glutaraldehyde, succinaldehyde or adipaldehyde. Of these, 1,4-butanediol diglycidyl ether, 1,6-hexanediol diglycidyl ether, adipic acid, adipoyl chloride and adipaldehyde are preferred. The crosslinkers react with the OH groups of the polysaccharides, and the crosslinked product obtained in this way is insoluble in water but swellable and dispersible in water and forms qualitatively good films.

The water uptake by the crosslinked polysaccharide, ie. the swelling of the crosslinked polysaccharide, is used for characterization. The crosslinked polysaccharides according to the invention have a swelling of from 100 to 1000%, preferably from 150 to 850%. The swelling is determined by weighing 100 mg of the crosslinked polysaccharides in the form of the polymer films into an ampoule and adding 10 ml of water. After 1, 5, 8, 20, 48 and 73 hours the film is removed from the water and dabbed on cellulose and weighed. The weight gain can be calculated by the following formula:

$$A = \frac{W_t - W_o}{W_o} \times 100$$

in which A is the percentage gain in weight, $W_o$ is the weight of the dry polymer and $W_t$ is the weight of the swollen polymer. In the present application the swelling is understood to be the value obtained when $W_t$ is constant.

The swelling depends slightly on the crosslinker. As indicated above, it is generally in the range from 100 to 1000%. When the diepoxides are used it is from 100% to 800%, preferably 200 to 400%. If dicarboxylic acids, their reactive derivatives and dialdehydes are used, the swelling is from 150 to 850%, preferably from 200 to 550%. The skilled person is easily able to establish by suitable preliminary tests what ratios of amounts of uncrosslinked polysaccharide and crosslinker must be used and whether the resulting crosslinked polymer has the properties according to the invention. The following examples indicate the ratios for crosslinking with diepoxides and with dicarboxylic acids or dialdehydes.

Crosslinkings with Diepoxides

In order to obtain the required crosslinked products for example on crosslinking of galactomannan with 1,4-butanediol diglycidyl ether and 1,6-hexanediol diglycidyl ether (diepoxides), the following ratios of the amounts of substances must be complied with. The ratios of the amounts of substances are based on the primary and secondary OH groups of the sugar building blocks. The products resulting from the crosslinking can be characterized on the basis of their swelling and stability in water and on the basis of their degradability by hemicellulases. Polysaccharides with insufficient crosslinking show excessive swelling or the films disintegrate. Polysaccharides with excessive crosslinking cannot any longer be broken down by the appropriate enzymes.

| Po | DiEp | NaOH | Crossl. time | Swelling | Film-form | Stabil. in H$_2$O | Degradability |
|----|------|-------|--------------|----------|-----------|-------------------|---------------|
| 1  | 3    | 0.001 | 140 min      | 800%     | yes       | low               | yes           |
| 1  | 3    | 0.02  | 150 min      | 550%     | yes       | +                 | yes           |
| 1  | 4    | 0.03  | 170 min      | 300%     | yes       | good              | yes           |
| 1  | 5    | 0.04  | 180 min      | 250%     | yes       | very good         | yes           |
| 1  | 5    | 0.06  | 300 min      | 150%     | moderate  | —                 | yes           |
| 1  | 5    | 0.1   | 300 min      | <100%    | no        | —                 | no            |

Notes: Po = polysaccharide, DiEp = diepoxide, the indicated ratios are ratios of amounts of substances.

All crosslinked products with a swelling of from 100% to 800%, preferably 200 to 400%, are broken down by hemicellulases. These crosslinked products are preferred when $C_4$–$C_{10}$-alkanediol diglycidyl ethers are used.

Crosslinkings with Dicarboxylic Acids and Dialdehydes

The following ratios of amounts of substances must be complied with in crosslinking with dicarboxylic acids, their reactive derivatives and dialdehydes. The ratios of amounts of substances are based on the primary and secondary OH groups in the sugar building blocks. The resulting products can be characterized by the swelling in water, the film-forming properties, the stability in water and the degradability with hemicellulases. Polysaccharides with excessive crosslinking cannot any longer be broken down.

| Po | DiCb/ DiCbcl | DCC | 4-DMAP | Crossl. time | Swelling | Film-form | Degradability |
|----|--------------|-----|--------|--------------|----------|-----------|---------------|
| 1  | 3.8          | 1.3 | —      | 24 h         | 850%     | yes       | yes           |
| 1  | 9.5          | 9.5 | —      | 24 h         | 730%     | yes       | yes           |
| 1  | 39.7         | 12  | —      | 24 h         | 630%     | yes       | yes           |
| 1  | 5.6          | 6   | —      | 48 h         | —        | no        | yes           |
| 1  | 0.48         |     | 1.2    | 12 h         | 534%     | yes       | yes           |
| 1  | 1            |     | 2      | 12 h         | 360%     | yes       | yes           |
| 1  | 2            |     | 4      | 20 h         | 300%     | yes       | yes           |
| 1  | 4            |     | 8      | 30 h         | 160%     | no        | yes           |

Notes: Po = polysaccharide, DiCb = dicarboxylic acid, DiCbcl = dicarbonyl chloride, 4-DMAP = 4-dimethylaminopyridine, DCC = dicyclohexylcarbodiimide.

The most important feature for characterization is the swelling of the crosslinked products and the enzymatic degradability. A strong ester band is evident at 1740 in the IR of polysaccharides crosslinked with dicarboxylic acids.

The films obtained from the crosslinked polysaccharides are insoluble in water but have various degrees of swelling in water which depend on the degree of crosslinking.

All these films are degradable both in the Freiburger large intestine microflora test, which is described hereinafter, and with pure β-mannanase or other exo/endoenzyme systems which occur in the large intestine. Release tests with films which swell only slightly and which were prepared from galactomannan as polysaccharide and 1,4-butanediol diglycidyl ether as crosslinker were able to show that release of a dye substance took place only after addition of the enzyme β-mannanase.

Crosslinked polyacrylates have already been used for this purpose by M. Saffran et al. (M. Saffran, G. S. Kumar, C. Savriar, J. C. Burnham, F. Williams and D. C. Neckers (1986): A new approach to the oral administration of Insulin and other peptide drugs, Science 233, 1081–1084). However, these did not show the desired effect. It was therefore surprising that the crosslinked polysaccharides made available according to the invention were usable for the said purpose. The crosslinked polysaccharides prepared by M. Saffran et al. were evidently crosslinked too much and insufficiently swellable so that they were broken down too slowly by the reductases in the large intestine microflora.

The invention likewise relates to a process for preparing the novel crosslinked polysaccharides as indicated above.

In the process according to the invention, the polysaccharide with the molecular weight indicated above is suspended in the crosslinker as indicated, with or without the addition of an inert solvent or swelling agent such an aliphatic alcohol. The absence of a solvent is preferred. The resulting suspension is heated while stirring to a temperature in the range from room temperature to 80° C., preferably to 60° C. The chosen temperature must not be so high that the polysaccharide forms aggregates. A catalytic amount of a base is added to the suspension. The nature of the base is not particularly important and, in general, alkali metal hydroxides such as sodium hydroxide or potassium hydroxide, alkali metal carbonates or organic bases such as, for example, 4-dimethylaminopyridine are used. However, it is also possible to use other bases. The reaction mixture is then stirred at room temperature or at a temperature of up to 80° C., preferably up to 60° C., particularly preferably up to 40° C., for a time of from 1 to 15 hours, preferably 1 to 6 hours. Subsequently, the crosslinked polysaccharide is removed in a manner known per se, for example by centrifugation, filtration etc. For purification, it is washed one or more times with water in a manner known per se. The product is dried and can then be used directly.

The novel crosslinked polysaccharides according to the invention can be used for coating or embedding medicinal active substances or drug compositions which are to be specifically used locally in the large intestine, or for protecting active substances which are normally broken down or digested under physiological conditions in the small intestine or in the stomach, or else for producing sheets which contain these medicinal active substances or drug compositions. In such cases it was hitherto necessary as a rule to administer the corresponding medicinal active substances parenterally.

It was surprising that the polysaccharides crosslinked according to the invention can be synthesized in one synthetic step, withstand the gastrointestinal tract undamaged and can be rapidly broken down in the large intestine.

The invention thus furthermore relates to the use of the crosslinked polysaccharides according to the invention for producing film coatings and embeddings of pharmaceutical active substances which can be administered orally and for which release of active substance is intended to take place in the large intestine. The medicinal active substances or drug compositions are coated with the crosslinked polysaccharides according to the invention and/or embedded in them. The coating or embedding takes place by processes known per se, described, for example, for coatings, in Bauer, Lehmann, Osterwald, Rothgang: Überzogene Arzneiformen, Wiss. Verlagsges. Stuttgart, 1988, and for embeddings in Bauer, Frömming, Führer: Pharmazeut. Technologie, 3rd edition, G. Thieme Verlag Stuttgart, 1991, pages 278,353 and 358.

It is possible, for example, to produce granules, pellets, tablets etc. in a manner known per se.

Suitable examples of active substances which can preferably be formulated with the crosslinked polysaccharides according to the invention are those medicinal active substances which are broken down or digested in the stomach or small intestine and therefore could not in the past be administered orally, and drugs intended not to act until the large intestine, such as drugs acting on disorders of the large intestine, and peptide drugs. Examples are: peptides, cardiovascular therapeutic agents, antirheumatics/analgesics, compositions for the therapy of disorders of the large intestine such Crohn's disease and ulcerative colitis, antiasthmatics, antifibrinolytics, antihemorrhagics, antitumor agents, enzyme products, antibiotics, antimycotics, substances acting on the central nervous system.

Examples of peptide active substances are: ACTH (adrenocorticotropic hormone), corticostatin, calcitonin, insulin, oxytocin, somatostatin and analogs, LHRH analogs, bombesin analogs, cholecystokinin and derivatives, endothelin and analogs, thrombin inhibitors, peptide growth factors (eg. IGF, EGF, NGF), magainins (PGS peptides), gastrin analogs, bradykinin analogs, parathormone analogs, neurokinin and analogs, VIP and analogs, ANP (atrial natriuretic peptide) and analogs, neokyotrophin and analogs, angiotensin analogs, enkephalins, dynorphins, dermorphins, deltorphins, renin-inhibiting peptides, tumor growth factor peptides, MSH (melanocyte stimulating hormone) analogs, mitotoxins, tyrphostins, chromogranin A, thymopentin, TRH and analogs, substance P, tuftsin, fibronectin, and peptide immunomodulators such as cyclosporin A, FK 506, neuropeptide Y and NPK.

Preferably used according to the invention are peptides prepared biotechnologically, in particular lower peptides.

The microflora test of A. Sarlikiotis (A. Sarlikiotis, J. Betzing, Ch. Wohlschlegel and K. H. Bauer (1992): A new in-vitro method for testing colon targeting drug delivery systems or excipients, in the press: Pharmaceutical and Pharmacological Letters, Springer Verlag International) was used to test crosslinked polysaccharides degradable in the large intestine and the resulting drugs.

The following examples illustrate the invention:

EXAMPLE 1

Crosslinking of galactomannan with 1,4-butanediol diglycidyl ether 2.0 g of spray-dried galactomannan are suspended in 26.7 g of 1,4-butanediol diglycidyl ether in an Erlenmeyer flask which can be closed. This suspension is heated to 50° C. After this temperature is reached (10 min), 3.5 ml of 0.2N NaOH are cautiously added dropwise. During this no or only slight aggregate formation should occur. This reaction mixture is left to stir at 50° C. until the end of the reaction period. After the reaction is complete, the suspension is centrifuged to remove the polymer. The crosslinked polysaccharide removed by centrifugation is subsequently washed several times with water. For further purification, the polymer is washed with acetone, lengthy stirring in acetone being beneficial. The crosslinked galactomannan obtained in this way can be dispersed in water with the aid of an Ultraturrax. Qualitatively good films can be produced from such aqueous dispersions. The minimum film-forming temperature is about 50° C., and the degree of swelling is from 400 to 600%.

EXAMPLE 2

Crosslinking of galactomannan with 1,6-hexanediol diglycidyl ether 2.0 g of spray-dried galactomannan are suspended in 26.7 g of 1,6-hexanediol diglycidyl ether in an Erlenmeyer flask which can be closed. This suspension is heated to 50° C. After this temperature is reached (10 min), 3.5 ml of 0.2N NaOH are cautiously added dropwise. During this no or only slight aggregate formation should occur. This reaction mixture is left to stir at 50° C. until the end of the reaction period. After the reaction is complete, the suspension is centrifuged to remove the polymer. The crosslinked polysaccharide removed by centrifugation is subsequently washed several times with water. For further purification, the polymer is washed with acetone, lengthy stirring in acetone being beneficial. The crosslinked galactomannan obtained in this way can be dispersed in water with the aid of an Ultraturrax. Qualitatively good films can be produced from such aqueous dispersions. The minimum film-forming temperature is about 50° C., and the degree of swelling is from 400 to 600%.

EXAMPLE 3

Crosslinking with adipic acid (a) 2.0 g of spray-dried galactomannan are suspended in 20.0 ml of absolute chloroform in a round-bottom flask. 29.0 g of adipic acid, which is less than the stoichiometric amount, and 41.0 g of dicyclohexylcarbodiimide as water-binding reagent are added to this suspension. This dispersion is refluxed at 60° C. for 48 hours. The suspension is subsequently filtered with suction and treated with about 500 ml of hot methanol in the Soxhlet process for 24 hours to remove the urea derivative which is formed. The polysaccharide product obtained in this way is insoluble in water but degradable with enzyme solution. The degree of swelling is about 400 to 600%.

(b) 2.0 g of spray-dried galactomannan are suspended in 20 ml of dimethylformamide in a round-bottom flask. 6.1 g of adipoyl chloride are added to this suspension. Subsequently 8.1 g of 4-dimethylaminopyridine, which is the amount equivalent to the acid chloride, are added. The reaction mixture is subsequently heated to 60° C. The mixture is left at this temperature for about 15 hours. The product obtained in this way is filtered off with suction and purified with about 500 ml of hot methanol in the Soxhlet process for several hours. The degree of swelling is 400 to 600%.

EXAMPLE 4

Crosslinking with Succinaldehyde 2.0 g of spray-dried galactomannan are suspended in 14.19 g of succinaldehyde in a round-bottom flask. An appropriate amount of dicyclohexylcarbodiimide is added as water-binding agent to this suspension, and furthermore 3.0 g of ammonium nitrate as catalyst. It is also possible to use anhydrous mineral acids such as sulfuric acid or else 2,4-dinitrobenzoic acid as catalyst. This reaction mixture is stirred tightly closed at 50° C. for about 15 hours. The product obtained in this way is filtered off with suction and treated with about 500 ml of hot methanol with the aid of a Soxhlet for 24 hours. The product purified in this way is dried in an oven at 50° C. The degree of swelling is 300 to 500%.

We claim:

1. A pharmaceutical composition which comprises an active substance which acts in the large intestine or an active substance which is broken down on passing through the stomach or small intestine, coated with or embedded in a polysaccharide selected from the group consisting of galactomannans, laminarin, pectins, arabinogalactans, xylans and glucomannans which is crosslinked with bifunctional crosslinkers and is no longer water soluble but is still biodegradable, has a swelling of from 100 to 1000%, where the swelling, which means the percentage gain in weight, is determined by the following equation:

$$A = \frac{W_t - W_o}{W_o} \times 100$$

in which A is the percentage gain in weight, $W_o$ is the weight of the dry polymer and $W_t$ is the weight of the swollen polymer saturated with water.

2. A composition as defined in claim 1, which comprises as active substance a peptide drug.

3. A composition as defined in claim 2, which is in the form of tablets, granules or capsules.

4. A method of coating and/or embedding medically active substances or drug compositions which comprises the step of coating or embedding said substances or compositions with a crosslinked polysaccharide as defined in claim 1.

5. A pharmaceutical composition which comprises an active substance which acts in the large intestine or an active substance which is broken down on passing through the stomach or small intestine, coated with or embedded in a crosslinked polysaccharide wherein the crosslinker is a member selected from the group consisting of aliphatic diglycidyl ethers, $C_4$–$C_{10}$-aliphatic dicarboxylic acids or their reactive derivatives or $C_4$–$C_{10}$-aliphatic dialdehydes.

6. A pharmaceutical composition which comprises an active substance which acts in the large intestine or an active substance which is broken down on passing through the stomach or small intestines, coated with or embedded in a crosslinked polysaccharide wherein the crosslinker is a member selected from the group consisting of 1,4-butanediol diglycidyl ether, 1,6-hexanediol diglycidyl ether, succinic acid, glutaric acid, adipic acid or their reactive derivatives, succinaldehyde, glutaraldehyde or adipaldehyde.

* * * * *